United States Patent
Koenen et al.

(10) Patent No.: US 10,254,273 B2
(45) Date of Patent: Apr. 9, 2019

(54) METHOD AND KIT FOR ASSESSMENT OF SODIUM CHANNEL-RELATED ANTI- OR PRO-ARRHYTHMIC POTENTIAL OF COMPOUNDS

(71) Applicant: RUPRECHT-KARLS-UNIVERSITAET HEIDELBERG, Heidelberg (DE)

(72) Inventors: Michael Koenen, Heidelberg (DE); Pessah Yampolsky, Vienna (AT); Patrick A. Schweizer, Heidelberg (DE); Dierk Thomas, Heidelberg (DE); Hugo A. Katus, Heidelberg (DE)

(73) Assignee: RUPRECHT-KARLS-UNIVERSITÄT HEIDELBERG, Heidelberg (DE)

( * ) Notice: Subject to any disclaimer, the term of this patent is extended or adjusted under 35 U.S.C. 154(b) by 0 days.

(21) Appl. No.: 15/505,212

(22) PCT Filed: Aug. 11, 2015

(86) PCT No.: PCT/EP2015/068433
§ 371 (c)(1),
(2) Date: Feb. 20, 2017

(87) PCT Pub. No.: WO2016/026732
PCT Pub. Date: Feb. 25, 2016

(65) Prior Publication Data
US 2017/0269064 A1    Sep. 21, 2017

(30) Foreign Application Priority Data
Aug. 21, 2014 (EP) ..................................... 14181787

(51) Int. Cl.
*G01N 33/50* (2006.01)
*G01N 33/68* (2006.01)
*A61K 31/4458* (2006.01)

(52) U.S. Cl.
CPC ..... *G01N 33/5061* (2013.01); *A61K 31/4458* (2013.01); *G01N 33/5073* (2013.01); *G01N 33/6872* (2013.01)

(58) Field of Classification Search
None
See application file for complete search history.

(56) References Cited

U.S. PATENT DOCUMENTS

2005/0037442 A1    2/2005  Wang

OTHER PUBLICATIONS

Anderson et al., N Engl J Med. Aug. 27, 1981;305(9):473-477 (Year: 1981).*
Rizzo et al., Cardiovasc Res. Sep. 1, 2012;95(4):409-418 (Year: 2012).*
Noorman et al., Heart Rhythm. Mar. 2013;10(3):412-419. (Year: 2013).*
Lawrence, C.L. et al., "Nonclinical proarrhythmia models: Predicting Torsades de Pointes." *Journal of Pharmacological and Toxicological Methods*, 2005, 52:46-59, doi:10.1016/j.vascn.2005.04.011.
Noorman, M. et al., "Remodeling of the cardiac sodium channel, connexin43, and plakoglobin at the intercalated disk in patients with arrhythmogenic cardiomyopathy." *Heart Rhythm*, Mar. 2013, 10(3):412-419, doi:10.1016/j.hrthm.2012.11.018.
Thomsen, M.B. et al., "Assessing the proarrhythmic potential of drugs: Current status of models and surrogate parametes of torsades de pointes arrhythmias." *Pharmacology & Therapeutics*, 2006, 112:150-170, doi:10.1016/j.pharmthera.2005.04.009.
Xi, B. et al., "Functional Cardiotoxicity Profiling and Screening Using the xCELLigence RTCA Cardio System." *JALA*, Dec. 2011, 16:415-421, doi:10.1016/j.jala.2011.09.002.

* cited by examiner

*Primary Examiner* — Daniel C Gamett
(74) *Attorney, Agent, or Firm* — Saliwanchik, Lloyd & Eisenschenk

(57) ABSTRACT

The present invention relates to an in vitro method for evaluating the anti- or pro-arrhythmic potential, cardiotoxicity and/or modulation capacity of cardiomyocyte function of compound(s). The present invention also relates to compound(s) identified or evaluated in the method of the invention for use in the treatment of a heart disease. The present invention further relates to the use of the density change of cardiac Nav 1.5 sodium channels in intercalated discs of cardiomyocytes as marker and/or diagnostic for the anti- or pro-arrhythmic potential of a compound, the cardiotoxicity of a compound or modulation capacity of cardiomyocyte function by said compound, and/or in preclinical assessment for cardiac liability of compounds and cardio-safety assessment. The present invention further relates to a kit for evaluating the anti- or pro-arrhythmic potential, cardiotoxicity and/or modulation capacity of cardiomyocyte function of compound(s).

16 Claims, 4 Drawing Sheets

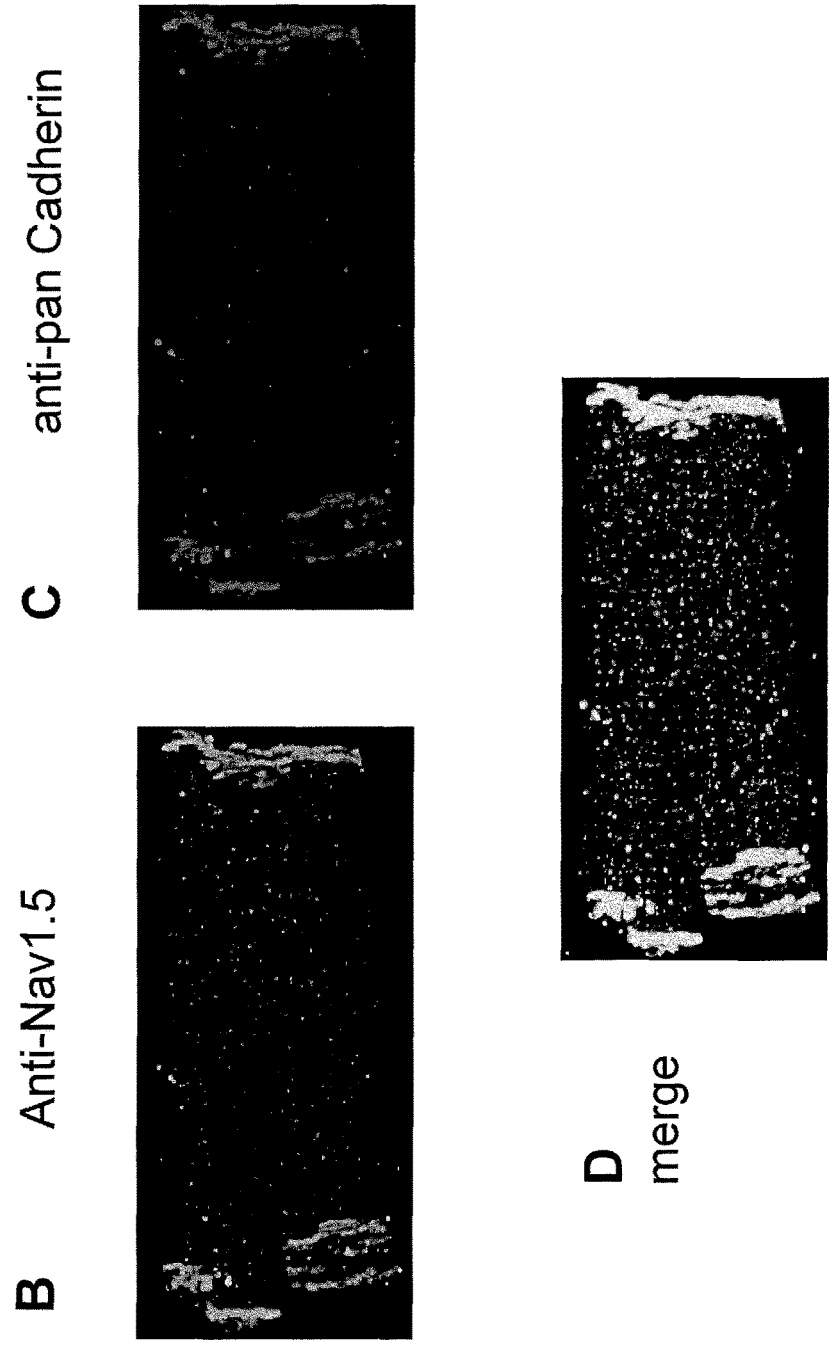
Figure 1 B - D

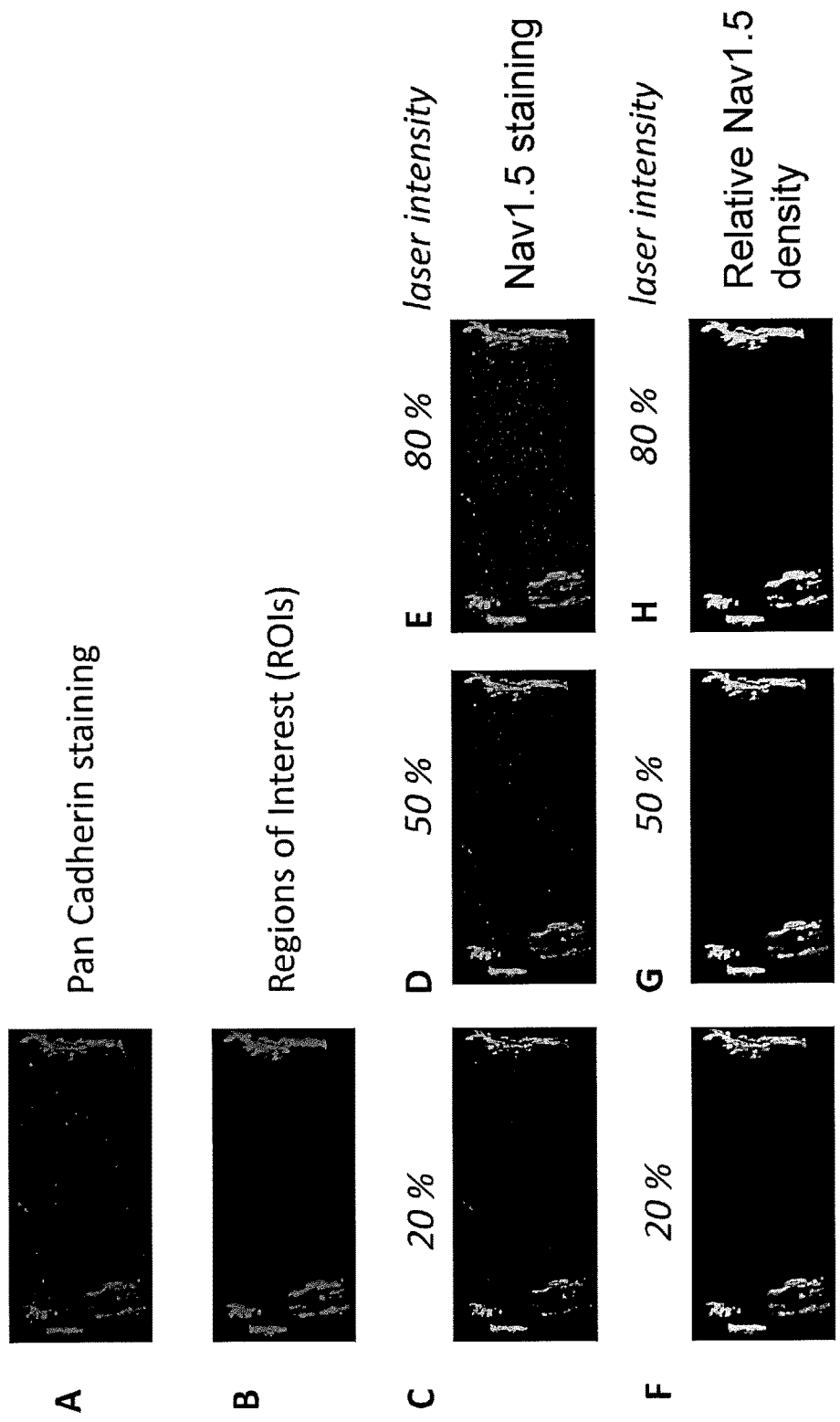
Figure 2 A - H

METHOD AND KIT FOR ASSESSMENT OF SODIUM CHANNEL-RELATED ANTI- OR PRO-ARRHYTHMIC POTENTIAL OF COMPOUNDS

CROSS REFERENCE TO A RELATED APPLICATION

This application is a National Stage Application of International Application Number PCT/EP2015/068433, filed Aug. 11, 2015; which claims priority to European Patent Application No. 14181787.4, filed Aug. 21, 2014; which are incorporated herein by reference in their entirety.

The present invention relates to an in vitro method for evaluating the anti- or pro-arrhythmic potential, cardiotoxicity and/or modulation capacity of cardiomyocyte function of compound(s). The present invention also relates to compound(s) identified or evaluated in the method of the invention for use in the treatment of a heart disease. The present invention further relates to the use of the density change of cardiac Nav1.5 sodium channels in intercalated discs of cardiomyocytes as marker and/or diagnostic for the anti- or pro-arrhythmic potential of a compound, the cardiotoxicity of a compound or modulation capacity of cardiomyocyte function by said compound, and/or in preclinical assessment for cardiac liability of compounds and cardio-safety assessment. The present invention further relates to a kit for evaluating the anti- or pro-arrhythmic potential, cardiotoxicity and/or modulation capacity of cardiomyocyte function of compound(s).

BACKGROUND OF THE INVENTION

Adverse drug side effects, such as cardiotoxicity, are a major concern in drug development and a major cause of drug withdrawal from the market. Therefore, cardiac safety testing of drug candidates is an important part of the drug discovery and development process. All new chemical compounds need to be subjected to preclinical assessment for cardiac liability, in particular for drug-induced ventricular arrhythmia.

A number of in vitro and in vivo assays have been established to assess the effect of candidate compounds on cardiac function. Preclinical safety studies have been described in particular for the human ether-a-go-go (hERG) channel that is involved in QT prolongation, a risk factor that may induce potentially fatal arrhythmia, known as torsade de pointes (TdP) (Brown, 2005). The current standard method for the study of interaction of pharmacological compounds with hERG is patch clamp analysis that records changes in the current density properties in heterologous cell expression systems. To date this is the single compulsory test, also known as the "hERG safety test", for the evaluation of cardiotoxicity as required by the guidelines of the drug development (Cavero & Crumb, 2005).

The need for the evaluation of further cardiac risk factors during drug development in addition to hERG, led to additional drug screening assays, such as the recent introduction of xCELLigence RCTA Cardio System (AVEA Biosciences, San Diego and Roche Applied Science). The assay provides valuable information in regard to cardiotoxicity by monitoring the contractility of cardiomyocytes based on impedance measurements (Xi et al., 2011) and thus allows a cardio-safety assessment.

There is a need in the art for improved means and methods for cardio-safety assessment.

SUMMARY OF THE INVENTION

According to the present invention this object is solved by an in vitro method for evaluating the anti- or pro-arrhythmic potential, cardiotoxicity and/or modulation capacity of cardiomyocyte function of compound(s), comprising the steps of:
(a) providing cardiomyocytes,
(b) incubating/culturing the cardiomyocytes of step (a);
(c) providing a compound to be tested;
(d) adding the compound of step (c) to the cardiomyocytes of step (b), and incubating the compound with the cardiomyocytes,
(e) detecting the intercalated discs of cardiomyocytes, and thereby determining the area of the intercalated discs in the cardiomyocyte(s),
(f) determining the density of the cardiac sodium channels Nav1.5 within said area of the intercalated discs,
(g) determining whether there is a density change of the cardiac sodium channels Nav1.5 in the area of the intercalated discs as detected/visualized/determined in step (e), by comparing the density of the cardiac sodium channels Nav1.5 determined in step (f) with the density determined in isolated cardiomyocytes where in step (d) no compound was added,
wherein a (relative) density change indicates that the tested compound has an anti- or pro-arrhythmic potential, cardiotoxicity and/or modulation capacity of cardiomyocyte function.

According to the present invention this object is solved by the use of the density change of cardiac sodium channels in intercalated discs of cardiomyocytes as marker/diagnostic for the anti- or pro-arrhythmic potential of a compound.

According to the present invention this object is solved by the use of the density change of cardiac sodium channels in intercalated discs of cardiomyocytes as marker/diagnostic for the cardiotoxicity of a compound or modulation capacity of cardiomyocyte function, such as cardiac arrhythmia, by said compound.

According to the present invention this object is solved by the use of the density change of cardiac sodium channels in intercalated discs of cardiomyocytes as in preclinical assessment for cardiac liability of compounds/cardio-safety assessment.

According to the present invention this object is solved by a kit or evaluating the anti- or pro-arrhythmic potential, cardiotoxicity and/or modulation capacity of cardiomyocyte function of compound(s), comprising
(i) means for detecting the intercalated discs of cardiomyocytes and determining the area of intercalated discs in the cardiomyocyte(s),
(ii) means for determining the density of the cardiac sodium channels Nav1.5,
(iii) means and/or instructions for determining the density change of the cardiac sodium channels Nav1.5 within said area of the intercalated discs,
such as respective software and/or computer hardware,
(iv) optionally, means and/or instruction for obtaining suitable cardiomyocytes, According to the present invention this object is solved by a compound identified or evaluated in a method of any of claims 1 to 10 as having an anti- or pro-arrhythmic potential, cardiotoxicity and/or modulation capacity of cardiomyocyte function for use in the treatment of a heart disease.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited.

In Vitro Methods for Evaluating the Anti- or Pro-Arrhythmic Potential, Cardiotoxicity and/or Modulation Capacity of Cardiomyocyte Function of Compound(s)

Sodium channelopathies represent a group of hereditary and acquired arrhythmia syndromes caused by a dysfunction of the depolarizing cardiac sodium channel Nav1.5. Patients with increased but also with decreased channel activity/sodium current are at risk for arrhythmogenic heart disease. In recent years various forms of cardiac arrhythmias were brought in connection with a dysfunction of the Nav1.5 channel, these include in particular: the Brugada syndrome, isolated cardiac conduction disorder, hereditary sinus node dysfunction, the long QT syndrome 3 and forms of familial atrial fibrillation. Substances that have an impact on the Nav1.5 channel(s) therefore represent a risk that can lead to adverse arrhythmogenic reactions in patients (Maguy et al., 2006). An evaluation of new substances as to their interaction with Nav1.5 is currently not required by the guidelines of the drug development and is not usually carried out systematically (Cavero & Crumb, 2005), however it would be highly beneficial for a comprehensive cardio-safety assessment.

As such any direct or indirect interaction of a compound resulting in a change of Nav1.5 channel population, especially at the intercalated disc, indicates that the tested compound affects scaffolding, trafficking, membrane integration, formation, maintenance and function of rhythmogenic Nav1.5 channel complexes by direct interaction or by interaction with at least one component essentially required for scaffolding, trafficking, membrane integration, formation, maintenance and function of Nav1.5 channel complexes. The finding of any interaction indicates that the tested compound has an anti- or pro-arrhythmic potential, cardiotoxicity and/or modulation capacity of cardiomyocyte function.

Functional changes of the sodium channel that occur within cardiomyocyte-specific processes (Watanabe et al., 2011) or only in the heteromeric channel configuration, may not be recorded in a heterologous expression assay because the cell types currently used for this purpose differ substantially from cardiomyocytes concerning their morphology and structure of subcellular compartments. In addition, "whole-cell" patch-clamp recordings of cardiomyocytes would not allow the mapping of the substance effect to the intercalated disks, a structure that is of primary importance with respect to cardiac conduction and arrhythmogenesis.

The present invention now provides methods and means for determining whether a test compound has such (direct or indirect) effect on the Nav1.5 channel(s) within the intercalated discs of cardiomyocytes.

As discussed above, the present invention provides an in vitro method for evaluating the anti- or pro-arrhythmic potential, cardiotoxicity and/or modulation capacity of cardiomyocyte function of compound(s).

Said method comprises the steps of:
(a) providing cardiomyocytes,
(b) incubating/culturing the cardiomyocytes of step (a);
(c) providing a compound to be tested;
(d) adding the compound of step (c) to the cardiomyocytes of step (b), and incubating the compound with the cardiomyocytes,
(e) detecting the intercalated discs of cardiomyocytes, and thereby determining the area of the intercalated discs in the cardiomyocyte(s),
(f) determining the density of the cardiac sodium channels Nav1.5 within said area of the intercalated discs,
(g) determining whether there is a density change of the cardiac sodium channels Nav1.5 in the area of the intercalated discs as detected/visualized/determined in step (e), by comparing the density of the cardiac sodium channels Nav1.5 determined in step (f) with the density determined in isolated cardiomyocytes where in step (d) no compound was added, wherein a (relative) density change indicates that the tested compound has an anti- or pro-arrhythmic potential, cardiotoxicity and/or modulation capacity of cardiomyocyte function.

Preferably, the cardiomyocytes are selected from
adult cardiomyocytes,
such as isolated from cardiac tissue of vertebrates, e.g. murine,
primary cardiomyocytes,
such as isolated from cardiac tissue of vertebrates, e.g. murine,
embryonic stem (ES) cell-derived cardiomyocytes,
induced pluripotent stem (iPS) cell-derived cardiomyocytes,
human adult cardiomyocytes,
such as derived from human biopsies or explanted human heart tissue,
human progenitor cell-derived cardiomyocytes,
human embryonic stem (hES) cell-derived cardiomyocytes,
human induced pluripotent stem (hiPS) cell-derived cardiomyocytes.

Preferably, in step (d) the conditions and/or parameters for adding the test compound can be varied.
Such as, the test compound is added in
different concentrations,
in different solvents,
in different culture media,
at different incubation temperatures,
at different times after cell preparation, and/or
in different intervals in pulse-chase analyses.

Preferably the detection of the intercalated discs of cardiomyocytes in step (e) is carried out by binding of at least one detection compound (for the intercalated discs of cardiomyocytes) to one or several components of the
adherens junction,
such as N-cadherin, plakoglobin, plakophilin, CAR, LIMP-2, vinculin, metavinculin, ZO-1, mXinα, α-actinin, α-E-catenin, α-T-catenin, β-catenin,
desmosome junction,
such as desmocollin, desmoglein, plakoglobin, β-catenin, plakophilin, desmoplakin, desmin, myozap,
intercalated disc associated protein-complex,
such as ankyrin G, synapse-associated protein 97 (SAP97), syntrophin/dystrophin, $Ca^{2+}$/calmodulin-dependent protein kinase II (CAMKII), connexin 43.

The at least one detection compound used in step (e) to detect the intercalated discs of cardiomyocytes is preferably selected from at least one of the following
labeled antibodies
preferably labeled primary antibodies,
such as labeled anti-cadherin antibody
or primary antibodies and labeled secondary antibodies,
such as anti-cadherin antibody and a secondary labeled antibody,
labeled nucleic acid aptameres,
labeled protein aptameres,
labeled protein binding substances,
such as natural or synthetic chemical compounds, e.g toxins
labeled viral proteins,
such as surface proteins of viruses, e.g. coxsackievirus, adenovirus,
and/or
tagged gene expression products of vectors,
such as fluorescent-labeled proteins or tagged proteins, e.g. GFP tag, His tag, FLAG tag, tetracystein tag.

In a preferred embodiment, the detection compound for detecting the intercalated discs of cardiomyocytes is a labeled anti-cadherin antibody or an anti-cadherin antibody and a secondary labeled antibody.

In step (e), at first the intercalated discs of cardiomyocytes are detected/visualized/measured. In one embodiment, such as when confocal microscopy is used, as further discussed below, the (fluorescence) signal (such as of a labeled anti-cadherin antibody or an anti-cadherin antibody and a secondary labeled antibody corresponding to the panCadherin staining) is digitally recorded using a confocal microscopy setup (according to Yampolsky et al., 2010, a). Thereby, the area of the intercalated discs in the cardiomyocyte(s) is determined, which can also be called the Region of Interest (ROI).

In one embodiment, when using a suitable image software, such as ImageJ software (NIH, free imaging software), the areas occupied by the (fluorescence signal) of the respective detection compound for the intercalated discs (such as panCadherin staining) are quantitatively determined, such as by using suitable built-in software function that measures the number of fluorescent pixels. The regions of interest (ROI) are set to the (fluorescence) signal of the respective detection compound for the intercalated discs (such as panCadherin staining), representing the intercalated disc areas.

Preferably, in step (f) the density of the cardiac sodium channels Nav1.5 is determined using at least one of the following detection compounds (for cardiac sodium channels Nav1.5)
labeled antibodies
preferably labeled primary antibodies,
such as labeled anti-Nav1.5 antibody
or primary antibodies and labeled secondary antibodies,
such as anti-Nav1.5 antibody and a secondary labeled antibody,
labeled nucleic acid aptameres,
labeled protein aptameres,
labeled protein binding substances,
such as natural or synthetic chemical compounds, e.g toxins
labeled viral proteins,
such as surface proteins of viruses, e.g. coxsackievirus, adenovirus, and/or
tagged gene expression products of vectors,
such as fluorescent-labeled proteins or tagged proteins, e.g. GFP tag, His tag, FLAG tag, tetracystein tag.

In a preferred embodiment, the detection compound for determining the density of the cardiac sodium channels Nav1.5 is a labeled anti-Nav1.5 antibody or an anti-Nav1.5 antibody and a secondary labeled antibody.

Preferably, the label(s) of the detection compounds (for intercalated discs or Nav1.5, respectively) are selected from:
fluorophores,
such as GFP, fluorescein, FITC, FlAsH, MFP (e.g. MFP488, MFP555),
radionuclides,
such as sulfur-35, phosphorus-32, carbon-14, iodine-125,
luminescent dyes,
such as luciferase,
and/or
enzymes,
such as HRP.

In a preferred embodiment, the labels are fluorophores, such as MFP dyes for confocal microscopy (e.g. MFP488, MFP555).

The method according to the invention preferably comprises imaging and/or detection via
microscopy,
such as confocal microscopy,
photostimulated luminescence,
such as phosphoimager, CCD camera based-imager, laser scanner,
radionuclide imaging,
such as radioactivity imager.

Preferably, determining the density of the cardiac sodium channels Nav1.5 within the area of the intercalated discs in step (f) comprises:
(1) detecting the area containing cardiac sodium channels Nav1.5 in the cardiomyocyte(s),
(2) determining the area of the intercalated discs which contain Nav1.5 channels,
more preferably by division of the value from step (1) by the value from step (e), namely the area of the intercalated discs in the cardiomyocyte(s) or ROI.

In one embodiment, such as when confocal microscopy is used, the Nav1.5 signal is sampled in images recorded at different incremental laser intensities, such as three incremental laser intensities, e.g. incremental laser intensities of 20%, 50% and 80% (according to Yampolsky et al., 2010, b).

In one embodiment, when using a suitable image software, such as Image software (NIH, free imaging software), the areas occupied by the fluorescence signal of the respective detection compound for Nav1.5 (such as Nav1.5 staining) are quantitatively determined, such as by using suitable built-in software function that measures the number of fluorescent pixels.

In one embodiment, the relative density of Nav1.5 channels in respective ROI is determined, and calculated, such as by using MS Excel.

Furthermore, preferably the slopes of pixel value change relative to laser intensity is calculated, averaged and used as a measure for relative Nav1.5 channel density in the intercalated disc.

For example:

ROI are as defined by the fluorescence signals of the cadherin staining, which represent the intercalated discs. The areas containing the fluorescence signal of Nav1.5 staining are measured separately in images recorded at 20%, 50% and 80% laser intensities, while applying the same threshold value (X) for all images (modified from Yampolsky et al., 2010, b). Nav1.5 density values $D_{20}$, $D_{50}$ and $D_{go}$ are calculated by division of respective area values containing Nav1.5 by the ROI area values as determined by measurement of the cadherin signals:

$D_{20}$: relative Nav1.5 density at 20% laser intensity =
$$\frac{\text{area of } Nav1.5 \text{ signal at threshold } X}{ROI \text{ area}}$$

$D_{50}$: relative Nav1.5 density at 50% laser intensity =
$$\frac{\text{area of } Nav1.5 \text{ signal at threshold } X}{ROI \text{ area}}$$

$D_{80}$: relative Nav1.5 density at 80% laser intensity =
$$\frac{\text{area of } Nav1.5 \text{ signal at threshold } X}{ROI \text{ area}}$$

The intensity-dependent linear slope of Nav1.5 fluorescence signal values are calculated for cardiomyocytes incubated with the test compounds as follows:

slope of Nav1.5 fluorescence signal values =
$$\left[\frac{(D_{80} - D_{50})}{80\% - 50\%} + \frac{(D_{50} - D_{20})}{50\% - 20\%} + \frac{(D_{80} - D_{20})}{80\% - 20\%}\right] : 3$$

The slope values calculated for cardiomyocytes treated with different concentrations of the test compounds are divided by the slope values for untreated cardiomyocytes:

Nav1.5 density change in % =
$$\frac{\text{slope of } Nav1.5 \text{ fluorescence signal values, treated}}{\text{slope of } Nav1.5 \text{ fluourescence signal values, untreated}} \times 100$$

The comparison of slope values provides information on the degree of change in Nav1.5 density as a result of interaction with the test compounds at different concentrations and indicates an impact of the compound on cardiac conduction.

In a preferred embodiment, the relative mean change of Nav1.5 density as a result of an interaction with the test compound(s) is calculated and compared to the mean Nav1.5 density in the untreated control sample. Using standard statistical methods, e.g. by a Student's t-test for a single pair comparison or by ANOVA followed by a post-hoc test, e.g. Tukey's test, for multiple pair comparisons, the significance of Nav1.5 density change as a result of treatment with the test compounds is determined and the p-values are calculated. According to the invention, a change in Nav1.5 density in the treated sample is considered "significant" when $p<0.05$ and indicates that the tested compound may yield a possible anti- or pro-arrhythmic potential, cardiotoxicity and/or modulation capacity of cardiomyocyte function.

In one embodiment, for example, such as when the test compound is the antiarrhythmic agent flecainide, the treatment of samples with the test compound in a concentration 100 μM or higher resulted in a significant change of the Nav1.5 density in comparison to the untreated sample (treated with concentration of 100 μM vs. untreated sample, $p<0.05$), indicating the capacity of the assay to detect compounds that interfere with cardiac rhythmogenicity.

A significant change (as described in Cavero & Crumb, 2005, see e.g. FIG. 4) in the density of Nav1.5 channels at the intercalated disc indicates that the tested compound affects scaffolding, trafficking, membrane integration, formation, maintenance and function of rhythmogenic Nav1.5 channel complexes by direct interaction or by interaction with at least one component essentially required for scaffolding, trafficking, membrane integration, formation, maintenance and function of Nav1.5 channel complexes. The finding of said interaction indicates that the tested compound has an anti- or pro-arrhythmic potential, and might be implicated in cardiotoxicity and/or modulation capacity of cardiomyocyte function.

Use of the Density Change of Cardiac Sodium Channels as Marker/Diagnostic

As discussed above, the present invention provides the use of the density change of cardiac sodium channels in intercalated discs of cardiomyocytes
- as marker/diagnostic for the anti- or pro-arrhythmic potential of a compound,
- as marker/diagnostic for the cardiotoxicity of a compound or modulation capacity of cardiomyocyte function, such as cardiac arrhythmia, by said compound, and/or
- in preclinical assessment for cardiac liability of compounds/cardio-safety assessment.

Preferably, the density change of the sodium channels Nav1.5 in the intercalated discs of cardiomyocytes is measured/determined.

Said density change is preferably determined as discussed above or according to the method of the present invention.

Preferably, the use according to the present invention comprises the quantitative in vitro determination of the density change of the sodium channels Nav1.5 in the intercalated discs of cardiomyocytes after interaction with a compound, more preferably by comparing the density of the sodium channels Nav1.5 in the intercalated discs of treated cardiomyocytes (i.e. cardiomyocytes to which a test compound was added) with the density of the sodium channels Nav1.5 in the intercalated discs of untreated cardiomyocytes (i.e. cardiomyocytes to which no test compound was added).

Preferably, the cardiomyocytes are selected from
- adult cardiomyocytes,
  - such as isolated from cardiac tissue of vertebrates, e.g. murine,
- primary cardiomyocytes,
  - such as isolated from cardiac tissue of vertebrates, e.g. murine,
- embryonic stem (ES) cell-derived cardiomyocytes,
- induced pluripotent stem (iPS) cell-derived cardiomyocytes,
- human adult cardiomyocytes,
  - such as derived from human biopsies or explanted human heart tissue,
- human progenitor cell-derived cardiomyocytes, human embryonic stem (hES) cell-derived cardiomyocytes, human induced pluripotent stem (hiPS) cell-derived cardiomyocytes.

Preferably (and as discussed above for the method), a relative mean change of Nav1.5 density as a result of an interaction with the test compounds is calculated and compared to the mean Nav1.5 density in the untreated control sample. Using standard statistical methods, e.g. by a Student's t-test for a single pair comparison or by ANOVA followed by a post-hoc test, e.g. Tukey's test, for multiple pair comparisons, the significance of Nav1.5 density change as a result of treatment with the test compounds is determined and the p-values are calculated. According to the invention, a change in Nav1.5 density in the treated sample is considered "significant" when $p<0.05$ and indicates that the tested compound may yield a possible anti- or pro-arrhythmic potential, cardiotoxicity and/or modulation capacity of cardiomyocyte function.

As discussed above, a significant change (as described in Cavero & Crumb, 2005, see e.g. FIG. 4) in the density of Nav1.5 channels at the intercalated disc indicates that the tested compound may affect scaffolding, trafficking, membrane integration, formation, maintenance and function of rhythmogenic Nav1.5 channel complexes by direct interaction or by interaction with at least one component essentially required for scaffolding, trafficking, membrane integration, formation, maintenance and function of Nav1.5 channel complexes. The finding of said interaction indicates that the tested compound could have an anti- or pro-arrhythmic potential, and might be implicated in cardiotoxicity and/or modulation capacity of cardiomyocyte function.

Kits for Evaluating the Anti- or Pro-Arrhythmic Potential, Cardiotoxicity and/or Modulation Capacity of Cardiomyocyte Function of Compound(s)

As discussed above, the present invention provides a kit for evaluating the anti- or pro-arrhythmic potential, cardiotoxicity and/or modulation capacity of cardiomyocyte function of compound(s).

Said kit comprises
(i) means for detecting the intercalated discs of cardiomyocytes and determining the area of intercalated discs in the cardiomyocyte(s),
(ii) means for determining the density of the cardiac sodium channels Nav1.5,
(iii) means and/or instructions for determining the density change of the cardiac sodium channels Nav1.5 within said area of the intercalated discs,
such as respective software and/or computer hard ware,
(iv) optionally, means and/or instruction for obtaining suitable cardiomyocytes, Preferably, the means (i) for detecting the intercalated discs of cardiomyocytes are selected from the detection compounds as defined herein above
preferably an anti-cadherin antibody,
such as a labeled anti-cadherin antibody,
or a primary anti-cadherin antibody and a secondary labeled antibody.

Preferably, the means (ii) for determining the density of the cardiac sodium channels Nav1.5 are selected from the detection compounds as defined herein above
preferably an anti-Nav1.5 antibody,
such as a labeled anti-Nav1.5 antibody,
or a primary anti-Nav1.5 antibody and a secondary labeled antibody.

Preferably, the labels of the detection compound(s) for detecting the intercalated discs of cardiomyocytes (e.g. anti-cadherin antibody or respective secondary antibody) and the labels of the detection compound(s) for determining the density of the cardiac sodium channels Nav1.5 (e.g. anti-Nav1.5 antibody or respective secondary antibody) are different from each other.

The labels are preferably selected from:
fluorophores,
such as GFP, fluorescein, FITC, FlAsH, MFP (e.g. MFP488, MFP555),
radionuclides,
such as sulfur-35, phosphorus-32, carbon-14, iodine-125,
luminescent dyes,
such as luciferase,
and/or
enzymes,
such as HRP, In a preferred embodiment, the labels are fluorophores, such as MFP dyes for confocal microscopy (e.g. MFP488, MFP555).

Use of the Identified or Evaluated Compounds

As discussed above, the present invention provides a compound identified or evaluated in a method according to the invention as having an anti- or pro-arrhythmic potential, cardiotoxicity and/or modulation capacity of cardiomyocyte function for use in the treatment of a heart disease, preferably
cardiac arrhythmias
such as
Brugada syndrome,
isolated cardiac conduction defect,
hereditary sinus node dysfunction,
congenital long QT syndrome 3,
drug-induced long QT syndrome,
hereditary atrial fibrillation,
cardiomyopathy,
failing heart
and/or
cardiac hypertrophy.

For example, the compound is selected from flecainide.

PREFERRED EMBODIMENTS OF THE INVENTION

The inventors have developed a sensitive and quantitative assay for testing the arrhythmogenic or rhythmogenic effect of a compound/drug/drug candidate.

In principle, it is possible that compounds that lead to a reduction of the Nav1.5 channel density in the intercalated discs exhibit both pro- and anti-arrhythmic effects (Haverkamp et al., 2000). Substances that are clinically used for antiarrhythmic drug therapy in patients without structural or ischemic heart disease, can be potentially dangerous when applied in patients with structural or ischemic heart disease (e.g. cardiomyopathy or myocardial infarction) (Echt et al., 1991; CAS Trial II Investigators, 1992), because here pro-arrhythmic effects can outweigh the positive action of the drug. Both effects (pro- and anti-arrhythmic) are achieved by a reduction of functional sodium channels, however, due to the underlying disease, it may occur that the same drug will result in a different outcome.

The present invention allows to reliably, sensitively, and quantitatively determine any interaction of a compound with the density of Nav1.5 channels in the intercalated discs (i.e. any direct or indirect interaction of said compound. Any evidence of interaction as identified by the assay represents a capacity of the test compound to take significant effect on the heart rhythm. This method is particularly suitable for screening of new and already known compounds with regard to a possible anti- or pro-arrhythmic or cardiotoxic potential. The finding of a significant interaction of a compound, whether direct or indirect, with the Nav1.5 channels, implies a potential pro-arrhythmic hazard and therefore should be carefully evaluated with regard to its future or current clinical application.

The present invention allows for the first time to investigate in detail the effect of a test compound dependent on specific test conditions (concentration, time intervals, media conditions etc.=, and thereby to characterize the compound's substance characteristics with regard to the sodium current, such as in form a dose-effect relation with an ED50 value.

The inventors would like to emphasize that any measured change in channel density is evidence that the tested compound has an effect on this critical component and, therefore, allows to draw conclusions regarding the effect(s) of the compound on the heart rhythm dependent on the test conditions. Hence, the potential limitations of the therapeutic potential in clinical applications of the test compound can be better evaluated and the risks for patients can be minimized. Thus, the present invention provides important means and methods for the preclinical phase of developing new medicines.

The following examples and drawings illustrate the present invention without, however, limiting the same thereto.

BRIEF DESCRIPTION OF THE DRAWINGS

FIGS. 2 and 3 show how the confocal pictures are evaluated.

The panCadherin staining (FIG. 2A) is used for determining the Regions of Interest (ROI) (FIG. 2B; red areas). The relative density of the Nav1.5 stainings at 20% (FIG. 2C), 50% (FIG. 2D) and 80% (FIG. 2E) laser intensity were determined in the ROI (F,G,H; yellow areas).

Figure 1:
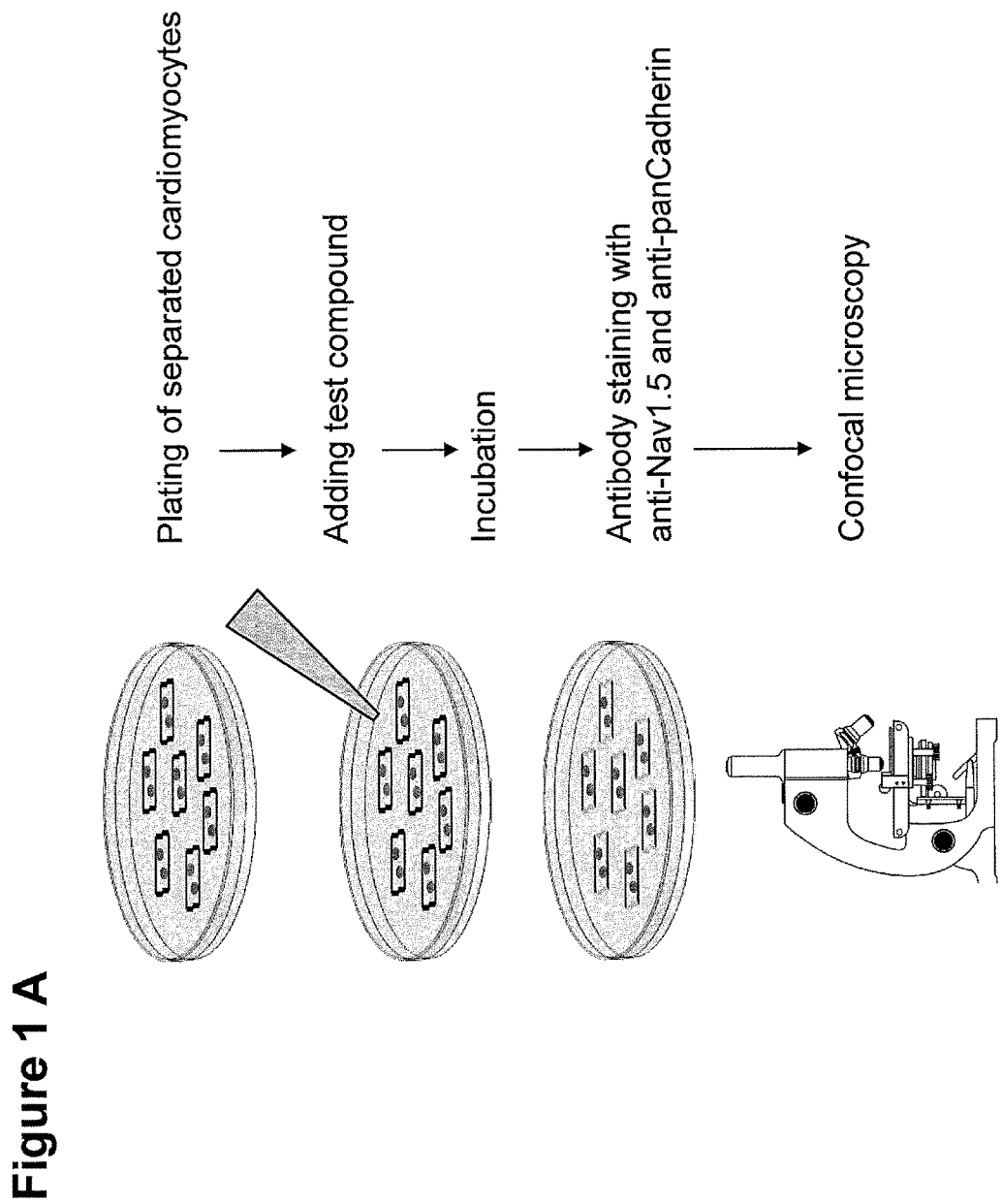
FIG. 1 schematically shows the steps of a preferred embodiment of the method according to the invention (A) for cultivating the cardiomyocytes in vitro, incubation with the compound to be tested, immunocytochemical staining with antibodies and confocal microscopy. Shown are the confocal picture of the Nav1.5 sodium channels (B) and panCadherin staining of the intercalated discs (C) as well as their merge (D).
Figure 3:
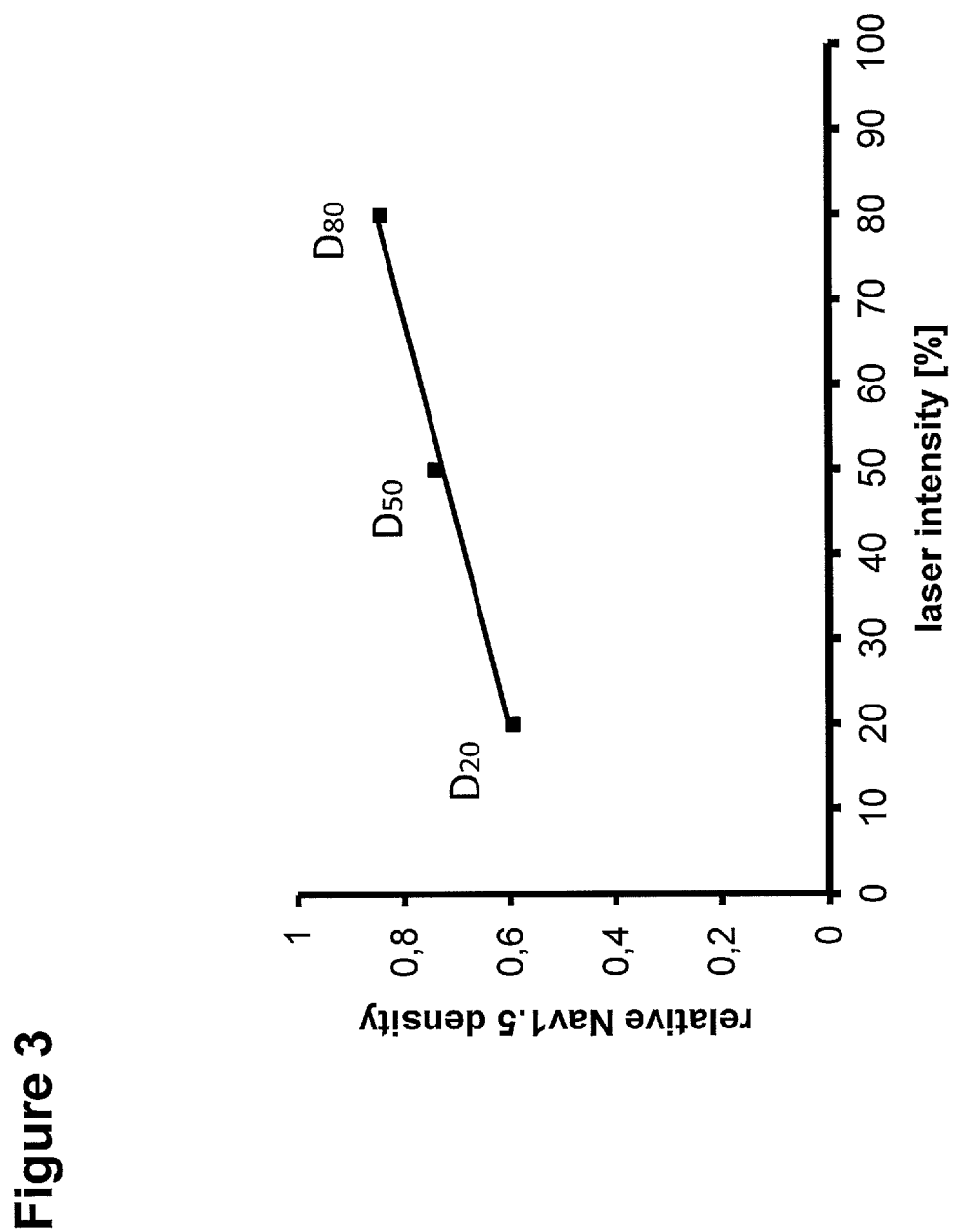

The $D_{20}$, $D_{50}$ and $D_{80}$ values of the relative Nav1.5 density are plotted in a xy-coordinate system (FIG. 3) for determining their intensity-dependent linear gradient.

EXAMPLES

Example 1

1. Material & Methods
1.1 Mouse Adult Cardiomyocyte Isolation

Cardiomyocytes isolation was performed largely according to Liao & Jain (2007). Briefly, the mice were injected with 200 IU heparin i.p. prior to sacrifice. The thoracic chamber was opened and a cannula with perfusion solution was inserted from the atria. The heart was harvested and perfused in the Langendorff system with Perfusion Buffer at 37° C. for 5 min, followed by Digestion Buffer until the heart muscle was pale and some signs of extracellular matrix dissociation appeared. The heart was perfused for additional 5 min with Perfusion Buffer to stop the dissociation. The cardiomyocytes were mechanically dissociated in TB-A and then plated on ECM-coated (Sigma cat. no. E-1270) petri dish (Zell-Kontakt cat. no. 5160-30). The extracellular calcium concentration was increased gradually in three consecutive steps from 0 mM (in TB-A) to 0.06 mM, 0.24 mM and 1.2 mM every 5 min. The cells were washed once with TB-B, transferred to round coverslips (on a 24-well cell culture plate; TPP cat. no. 92024) in Plating Medium. After 1 h incubation in a cell incubator at 37° C. at 5% $CO_2$ the medium was changed to Culture Medium and all further experiments were perforated in Culture Medium under the same conditions.

Solutions (Indications in mM):
- Perfusion Buffer: 135 NaCl, 4 KCl, 1 $MgCl_2$, 10 HEPES, 0.33 $NaH_2PO_4$, 10 glucose, 20 2,3-butanediones monoxime (Sigma cat. no. B0753), 5 Taurine, pH7.2 at 37° C.
- Digestion Buffer: 0.3 mg/g body weight collagenase D (Roche cat. no. 11088858001), 0.4 mg/g body weight collagenase B (Roche cat. no. 11088807001) and 0.05 mg/g body weight protease XIV (Sigma cat. no. P5147) in 25 ml Perfusion Buffer.
- Transfer Buffer A (TB-A): 135 NaCl, 4 KCl, 1 $MgCl_2$, 10 HEPES, 0.33 $NaH_2PO_4$, 5.5 glucose, 10 2,3-butanediones monoxime (Sigma cat. no. B0753), 5 mg/ml bovine serum albumin (Sigma cat. no. A6003), pH7.4 at 37° C.
- Transfer Buffer B (TB-B): 137 NaCl, 5.4 KCl, 1.8 $CaCl_2$, 0.5 $MgCl_2$, 10 HEPES, 5.5 glucose, pH 7.4 at 37° C.
- Plating Medium: Minimal Essential Medium, 100 U/ml penicillin-streptomycin, 2 L-glutamine, 10 2,3-butanedione monoxime (Sigma cat. no. B0753), 5% fetal calf serum.
- Culture Medium: Minimal Essential Medium, 100 U/ml penicillin-streptomycin, 2 L-glutamine, 0.1 mg/ml bovine albumin (Sigma cat. no. A6003).

1.2 Application of Chemical Compounds to Cardiomyocytes in Culture

Chemical or pharmaceutical compounds, e.g. fleicainide (Sigma Aldrich cat. no. F0120000), ajmaline (MP Biomedicals cat. no. 05212414), were dissolved in Culture Medium at 5 different concentrations, such as 0.01 mM, 0.1 mM, 1 mM, 10 mM, 100 mM, and applied to cardiomyocytes in 5 different wells, respectively. At the same time the medium in a control well was replaced with fresh Culture Medium. The cells were further incubated for up to 8 h in a cell incubator at 37° C. at 5% $CO_2$.

1.3 Immuncytochemistry

For immuncytochemical detection of intercalated discs and Nav1.5 cardiac sodium channels cardiomyocytes were fixed in 0.5% TritonX/PBS for 10 min, followed by incubation in 0.1M glycin/PBS for 1 h. Cardiornyocytes were blocked with 2% BSA/PBS (bovine serum albumin Sigma cat. no. A6003) for 1 h and incubated with a solution composed of 1:50 anti-Nav1.5 (Alomone Labs cat. no. ASC-005) and 1:500 anti-panCadherin (Abeam cat. no. ab22744) in 2% BSA/PBS overnight. The next day cells were washed with PBS for 15 min and incubated with a 1:500 dilution of labeled secondary antibodies MFP-A1034 and MFP-A2424 (MoBiTec) in 2% BSA/PBS for 4 h at room temperature. The cells were washed with PBS for 15 min, the coverslips with cells were mounted on a microscope slide in AF1 antifadent mountant solution (Citifluor).

1.4 Confocal Microscopy and Image Processing

Confocal images of red and green immunofluorescence of stained cardiomyocytes were acquired, e.g. on a Leica confocal laser scanning unit TCS NT, which is coupled to a Leica DM IRB microscope. Acquisition of image series was performed, e.g. using TCS NT (Leica, Hedelberg, Germany) software. Fluorescence signals of Nav1.5 staining were recorded at 20%, 50% and 80% laser intensity, and fluorescence signals of cadherin was recorded at 80% laser intensity to generate the Region of Interest (ROI) (modified from Yampolsky et al., 2010, a). All images were digitally saved and later processed with Image) (NIH, Bethesda, Md., USA) software using proprietary quantification methods and standard Image) plug-ins.

1.5 Image Quantification and Nav1.5 Density Change Assessment

ROI were set as defined by the fluorescence signals of the cadherin staining, which represented the intercalated discs. The areas containing the fluorescence signal of Nav1.5 staining were measured separately in images recorded at 20%, 50% and 80% laser intensities, while applying the same threshold value (X) for all images (modified from Yampolsky et al., 2010, b). Nav1.5 density values $D_{20}$, $D_{50}$ and $D_{80}$ were calculated by division of respective area values containing Nav1.5 by the ROI area values as determined by measurement of the cadherin signals:

$D_{20}$: relative *Nav*1.5 density at 20% laser intensity =
$$\frac{\text{area of } Nav1.5 \text{ signal at threshold } X}{ROI \text{ area}}$$

$D_{50}$: relative *Nav*1.5 density at 50% laser intensity =
$$\frac{\text{area of } Nav1.5 \text{ signal at threshold } X}{ROI \text{ area}}$$

$D_{80}$: relative *Nav*1.5 density at 80% laser intensity =
$$\frac{\text{area of } Nav1.5 \text{ signal at threshold } X}{ROI \text{ area}}$$

The intensity-dependent linear slope of Nav1.5 fluorescence signal values was calculated for cardiomyocytes incubated with the test compounds as follows:

slope of *Nav*1.5 fluorescence signal values =
$$\left[\frac{(D_{80}-D_{50})}{80\%-50\%} + \frac{(D_{50}-D_{20})}{50\%-20\%} + \frac{(D_{80}-D_{20})}{80\%-20\%}\right] : 3$$

The slope values calculated for cardiomyocytes treated with different concentrations of the test compounds were divided by the slope values for untreated cardiomyocytes:

*Nav*1.5 density change in % =
$$\frac{\text{slope of } Nav1.5 \text{ fluorescence signal values, treated}}{\text{slope of } Nav1.5 \text{ fluourescence signal values, untreated}} \times 100$$

The comparison of slope values provides information on the degree of change in Nav1.5 density as a result of interaction with the test compounds at different concentrations and indicates an impact of the compound on cardiac conduction.

The features disclosed in the foregoing description, in the claims and/or in the accompanying drawings may, both separately and in any combination thereof, be material for realizing the invention in diverse forms thereof.

REFERENCES

Brown A M. HERG block, QT liability and sudden cardiac death. Novartis Found Symp. 2005; 266:118-31; discussion 131-5, 155-8. Review.

Cavero I, Crumb W. ICH S7B draft guideline on the non-clinical strategy for testing delayed cardiac repolarisation risk of drugs: a critical analysis. Expert Opin Drug Saf. 2005 May; 4(3):509-30.

CAS Trial II Investigators. Effect of the antiarrhythmic agent moricizine on survival after myocardial infarction. N Engl J Med, 327(4), 227-33, (1992).

Echt D S, Liebson P R, Mitchell L B, Peters R W, Obias-Manno D, Barker A H, . . . & Richardson D W. Mortality and morbidity in patients receiving encainide, flecainide, or placebo: the Cardiac Arrhythmia Suppression Trial. New England Journal of Medicine, 324(12), 781-788, (1991).

Haverkamp W, Eckardt L, Kirchhof P, Mönnig G, Schulze-Bahr E, Wedekind H, Borggrefe M, Madeja M, Breithardt G. New knowledge in arrhythmogenesis—role of ion channels and genetic aspects. Z Kardiol. 2000; 89 Suppl 10:2-9; discussion 9-10. Review.

Liao, R., Jain, M. Isolation, culture, and functional analysis of adult mouse cardiomyocytes. Methods in Molecular Medicine. 139:251-62 (2007).

Maguy A, Hebert T E, Nattel S. Involvement of lipid rafts and caveolae in cardiac ion channel function. Cardiovasc Res. 2006 Mar. 1; 69(4):798-807.

Watanabe H, Yang T, Stroud D M, Lowe J S, Harris L, Atack T C, Wang D W, Hipkens S B, Leake B, Hall L, Kupershmidt S, Chopra N, Magnuson M A, Tanabe N, Knollmann B C, George A L Jr, Roden D M. Striking In vivo phenotype of a disease-associated human SCN5A mutation producing minimal changes in vitro. Circulation. 2011 Aug. 30; 124(9):1001-11.

Yampolsky, P., Pacifici, P. G., Witzemann, V. Differential muscle-driven synaptic remodeling in the neuromuscular junction after denervation. European Journal of Neuroscience, 31(4), 646-658, (2010, a).

Yampolsky, P., Pacifici, P. G., Lomb, L., Giese, G., Rudolf, R., Roder, I. V., Witzemann, V. Time lapse in vivo visualization of developmental stabilization of synaptic receptors at neuromuscular junctions. Journal of Biological Chemistry, 285(45), 34589-34596, (2010, b).

Xi B, Wang T, Li N, Ouyang W, Zhang W, Wu J, Xu X, Wang X, Abassi Y A. Functional cardiotoxicity profiling and screening using the xCELLigence RTCA Cardio System. J Lab Autom. 2011 December; 16(6):415-21.

The invention claimed is:

1. An in vitro method for evaluating the anti- or pro-arrhythmic potential, cardiotoxicity and/or modulation capacity of cardiomyocyte function of compound(s), comprising the steps of
(a) providing cardiomyocytes,
(b) incubating/culturing the cardiomyocytes of step (a);
(c) providing a compound to be tested;
(d) adding the compound of step (c) to the cardiomyocytes of step (b),
and incubating the compound with the cardiomyocytes,
(e) detecting the intercalated discs of cardiomyocytes, and thereby determining the area of the intercalated discs in the cardiomyocyte(s),
(f) determining the density of the cardiac sodium channels Nav1.5 within said area of the intercalated discs, and (g) determining whether there is a density change of the cardiac sodium channels Nav1.5 in the area of the intercalated discs as determined in step (e),
by comparing the density of the cardiac sodium channels Nav1.5 determined in step (f) with the density determined in isolated cardiomyocytes where in step (d) no compound was added,
wherein a relative density change indicates that the tested compound has an anti- or pro-arrhythmic potential, cardiotoxicity and/or modulation capacity of cardiomyocyte function.

2. The method of claim 1, wherein the cardiomyocytes are selected from
adult cardiomyocytes,
primary cardiomyocytes,
embryonic stem (ES) cell-derived cardiomyocytes,
induced pluripotent stem (iPS) cell-derived cardiomyocytes,
human adult cardiomyocytes,
human progenitor cell-derived cardiomyocytes,
human embryonic stem (hES) cell-derived cardiomyocytes, and
human induced pluripotent stem (hiPS) cell-derived cardiomyocytes.

3. The method, according to claim 2, wherein said adult cardiomyocytes and primary cardiomyocytes are isolated from cardiac tissue of a vertebrate; and the human adult cardiomyocyte is derived from a human biopsy or explanted human heart tissue.

4. The method of claim 1, wherein in step (d) conditions and/or parameters for adding the test compound are varied, such that the test compound is added
in different concentrations,
in different solvent,
in different culture media,
at different incubation temperatures,
at different times after cell preparation, and/or
in different intervals in pulse-chase analyses.

5. The method of claim 1, wherein the detection of the intercalated discs of cardiomyocytes in step (e) is carried out by binding of at least one detection compound to one or several components of the
adherens junction,
desmosome junction, and/or
intercalated disc associated protein-complex.

6. The method, according to claim 5, wherein the adherens junction is selected from N-cadherin, plakoglobin, plakophilin, CAR, LIMP-2, vinculin, metavinculin, ZO-1, mXinα, α-actinin, α-E-catenin, α-T-catenin, and β-catenin; the desmosome junction is selected from desmocollin, desmoglein, plakoglobin, β-catenin, plakophilin, desmoplakin, desmin, and myozap; and the intercalated disc associated protein-complex is selected from ankyrin G, synapse-associated protein 97 (SAP97), syntrophin/dystrophin, $Ca^{2+}$/calmodulin-dependent protein kinase II (CAMKII), and connexin 43.

7. The method of claim 5, wherein the at least one detection compound used in step (e) to detect the intercalated discs of cardiomyocytes is selected from:
labeled antibodies,
labeled nucleic acid aptameres,
labeled protein aptameres,
labeled protein binding substances
labeled viral proteins, and
tagged gene expression products of vectors.

8. The method of claim 7, wherein the label(s) of the detection compounds are selected from:
fluorophores,
radionuclides,
luminescent dyes and
enzymes.

9. The method of claim 1, wherein in step (f) the density of the cardiac sodium channels Nav1.5 is determined using at least one of the following detection compounds:
labeled antibodies,
labeled nucleic acid aptameres,
labeled protein aptameres,
labeled protein binding substances and
tagged gene expression products of vectors.

10. The method of claim 1, comprising imaging/detection via
microscopy,
photostimulated luminescence, and
radionuclide imaging.

11. The method of claim 1, wherein determining the density of the cardiac sodium channels Nav1.5 within the area of the intercalated discs in step (f) comprises:
(1) detecting the area containing cardiac sodium channels Nav1.5 in the cardiomyocyte(s), and/or
(2) determining the area of the intercalated discs which contain Nav1.5 channels.

12. A method for
assessing anti- or pro-arrhythmic potential of a compound,
assessing cardiotoxicity of a compound or modulation capacity of cardiomyocyte function, and/or
preclinical assessment for cardiac liability of compounds/cardio-safety assessment;
wherein said method utilizes the density change of cardiac sodium channels in intercalated discs of cardiomyocytes.

13. The method of claim 12, wherein the density change of the sodium channels Nav1.5 in the intercalated discs of cardiomyocytes is determined.

14. The method of claim 12, comprising the quantitative in vitro determination of the density change of the sodium channels Nav1.5 in the intercalated discs of cardiomyocytes after interaction with a compound by comparing the density of the sodium channels Nav1.5 in the intercalated discs of treated cardiomyocytes with the density of the sodium channels Nav1.5 in the intercalated discs of untreated cardiomyocytes.

15. The method of claim 12, wherein the cardiomyocytes are selected from
adult cardiomyocytes,
primary cardiomyocytes,
embryonic stem (ES) cell-derived cardiomyocytes,
induced pluripotent stem (iPS) cell-derived cardiomyocytes,
human adult cardiomyocytes,
human progenitor cell-derived cardiomyocytes,
human embryonic stem (hES) cell-derived cardiomyocytes, and
human induced pluripotent stem (hiPS) cell-derived cardiomyocytes.

16. A kit for evaluating the anti- or pro-arrhythmic potential, cardiotoxicity and/or modulation capacity of cardiomyocyte function of compound(s), comprising
(i) a labeled anti-cadherin antibody, or a primary anti-cadherin antibody and a secondary labeled antibody, for detecting intercalated discs of cardiomyocytes and determining the area of intercalated discs in the cardiomyocyte(s), (ii) a labeled anti-Nav1.5 antibody, or a primary anti-Nav1.5 antibody and a secondary labeled antibody, for determining the density of the cardiac sodium channels Nav1.5,
(iii) means and/or instructions for determining the density change of the cardiac sodium channels Nav1.5 within said area of the intercalated discs, and
(iv) optionally, means and/or instruction for obtaining suitable cardiomyocytes, wherein the labels of (i) for detecting the intercalated discs of cardiomyocytes and the labels of (ii) for determining the density of the cardiac sodium channels Nav1.5 are different from each other, and
the kit furthermore comprises flecainide.

* * * * *